United States Patent
Chaiken et al.

(10) Patent No.: US 7,664,605 B2
(45) Date of Patent: Feb. 16, 2010

(54) ABSOLUTE CALIBRATION PROCESS AND DEVICE FOR A TISSUE MODULATED RAMAN SPECTROMETER

(75) Inventors: Joseph Chaiken, Fayetteville, NY (US); Pamela J. Hagrman, Syracuse, NY (US); Dhyaneshwar Bhujangarao Chawan, Liverpool, NY (US); Douglas Hagrman, Syracuse, NY (US)

(73) Assignee: LighTouch Medical, Inc., Bryn Athyn, PA (US)

( * ) Notice: Subject to any disclaimer, the term of this patent is extended or adjusted under 35 U.S.C. 154(b) by 498 days.

(21) Appl. No.: 10/986,673

(22) Filed: Nov. 12, 2004

(65) Prior Publication Data

US 2005/0106651 A1    May 19, 2005

Related U.S. Application Data

(60) Provisional application No. 60/519,452, filed on Nov. 12, 2003.

(51) Int. Cl.
- *G01N 33/48* (2006.01)
- *G01N 31/00* (2006.01)
- *G01N 33/38* (2006.01)
- *C12Q 1/54* (2006.01)
- *C12M 1/00* (2006.01)
- *G01N 1/00* (2006.01)

(52) U.S. Cl. .............................. 702/19; 702/22; 435/14; 435/283.1; 422/50

(58) Field of Classification Search ........................ None
See application file for complete search history.

(56) References Cited

U.S. PATENT DOCUMENTS

| 6,475,800 B1 | 11/2002 | Hazen et al. |
| 6,485,703 B1 * | 11/2002 | Cote et al. .................. 424/9.1 |

FOREIGN PATENT DOCUMENTS

WO    WO01/15596 A1    3/2001

OTHER PUBLICATIONS http:\\www.nist.gov/public_affairs/update/upd20020826.htm; Aug. 26, 2002, pp. 1-6.

* cited by examiner

*Primary Examiner*—Eric S DeJong
(74) *Attorney, Agent, or Firm*—Karen S. Canady; Canady + Lortz LLP

(57) ABSTRACT

A calibrator suitable for calibrating a noninvasive analyte detector, such as a Raman spectroscopy device, allows the user of the detection device to establish standard measurements of the analyte to be detected, thereby providing assurance that appropriate analyte measurements are obtained at the time of sampling. The calibrator is simple to use, making it suitable for home use by individuals regardless of medical or technical skill level. In particular, the calibrator can be used with a noninvasive glucose detection system, such as for monitoring of blood glucose levels in diabetics. For use with noninvasive detectors designed for obtaining measurements from a subject's fingertip, the calibrator can be formed into a shape that reasonably mimics a fingertip in size, texture and/or spectral properties.

14 Claims, 1 Drawing Sheet

ABSOLUTE CALIBRATION PROCESS AND DEVICE FOR A TISSUE MODULATED RAMAN SPECTROMETER

This application claims benefit of U.S. provisional patent application No. 60/519,452, filed on Nov. 12, 2003, the entire contents of which are incorporated herein by reference. Throughout this application various publications are referenced. The disclosures of these publications in their entireties are hereby incorporated by reference into this application in order to more fully describe the state of the art to which this invention pertains.

BACKGROUND OF THE INVENTION

Precise measurements of Raman spectra are necessary to help obtain accurate, corrected, reliable data on the relative intensity of these spectra, obtained by instruments that employ light of a set wavelength. Assuring accuracy in measurements is essential to research in many branches of optical physics, analytical chemistry, and allied fields; and particularly in the pharmaceutical industry and the forensics community for validation of the performance of their instruments.

NIST announces reference values for correcting the relative intensity of Raman spectra obtained with instruments that use 785-nm laser excitation in its SRM 2241 Relative Intensity Correction Standard for Raman Spectroscopy. SRM 2241 consists of an optical glass that emits a broadband luminescence spectrum when it is excited with 785-nm laser radiation. The shape of the luminescence of this glass is described by a polynomial expression that relates the relative spectral intensity to the wave number ($cm^{-1}$), expressed as the Raman shift from the excitation wavelength of 785-nm. Together with a measurement of the luminescence spectrum of the standard, this polynomial can be used to determine the spectral intensity response correction that is unique to each Raman system.

The relative spectral intensity of the glass luminescence was determined through the use of a white-light, uniform-source, integrating sphere that has been calibrated for its irradiance at NIST. The instrument-intensity response correction obtained with this standard may be used to obtain Raman spectra that are instrument-independent.

SRM 2241 is intended for use in measurements over the range of 20° C.-25° C. and with Raman systems that use laser excitation at 785-nm. It also may be used for Raman excitation with lasers that range from 784-nm to 786-nm in excitation wavelength. SRM 2241 can be purchased from National Institute of Standards and Technology, Standard Reference Materials Group, 100 Bureau Drive, Stop 2322, Gaithersburg, Md. 20899-2322.

In fact, there are about as many different kinds of standards for analytical instruments as there are different kinds of instruments. SRM2241 is a material that was designed to allow standardization of Raman spectra obtained on different machines so that published spectra from different machines can be directly compared with each other. This material can be fabricated into many shapes and sizes so that it is compatible with use in various machines ranging from commercial Raman spectrometers that use cuvettes as sample holders to Raman microscopes that use microscope slides as sample holders.

Calibration standards are included with commercial finger stick based glucometers (FSGs) that permit verification of glucometer operation. Such FSG standards take the form of solutions that can be introduced into the same cuvettes that normally hold sample, i.e. capillary blood obtained via fingerstick. This approach succeeds for many analytical devices when the sample preparation and the physical form of the calibrator material can be made sufficiently similar to the intended unknown samples that virtually all the sources for error and or imprecision are checked by use of the calibrator.

SRM2241 and similar or derived materials and devices allow the user to test and calibrate the wavenumber and detection sensitivity of generic Raman instruments. However, a preferred system for noninvasive glucose monitoring, the LighTouch™ glucometer, relies on the operation of a Raman spectrometer system and also on a tissue modulation system. A LightTouch™ calibrator intended for use by lay people involved in self-monitoring of blood glucose must allow easy and safe testing of both subsystems.

The invention disclosed herein relates to novel ways to incorporate SRM2241 and similar materials into a calibrator appropriate to a user-friendly, noninvasive monitoring system, such as the LightTouch™ measurement paradigm. Also disclosed are novel calibrators unrelated to the material SRM 2241, but each having its own specific characteristic advantages for certain types of commercial systems. Multiple approaches to calibrator design are advantageous in anticipation of the continued evolution of noninvasive in vivo monitoring devices.

Noninvasive in vivo glucometers present a unique concern in that the sample holder must interface between a sensitive spectrometer and some portion of a human body. Few objects are as variable in shape and texture as the fully differentiated and integrated tissue and organ systems present in virtually any portion of the human body. The relevant portion of the human body can be regarded as a highly spatially and temporally variable optical medium. The calibrator/sample must produce a spectroscopic response that, when subjected to the same signal processing and data extraction algorithm(s) employed for handling in vivo tissue, produces a correct result. The calibrator must interact with the tissue modulation system in a manner that causes the LightTouch™ device to initiate and perform a measurement cycle.

In one embodiment of the LightTouch™ device, a measurement cycle is initiated in response to placing a particular volar side fingertip capillary bed in juxtaposition with an orifice. The proper positioning of the fingertip causes the switching of an aperture, un-shuttering the laser and providing a required eye safety function. Proper positioning is sensed by the LightTouch™ device using various measurements including, but not limited to, the average and temporal pressure/force variation on the orifice. The software and hardware of the system that interface to the sample must also function properly with either the calibrator or the in vivo sample to produce the correct answer. As disclosed herein, it is possible, using these two observables, to automatically discern between a calibration measurement cycle and a real in vivo measurement cycle.

Some noninvasive spectroscopic blood analysis strategies involve comparing a measurement of a specific person's spectroscopic response to some function of their own earlier measurements. In this way, that device is considered calibrated to that individual. One could certainly design an embodiment of some material which could be used to test the operation of the spectroscopic system of such non-tissue modulated, noninvasive glucometers. Given an appropriate material to serve as sample, the algorithm itself suggests tests that would probe the operation of the internal calibration system. There might be some induction period needed to provide some prior data for internal comparison, but other approaches might be adequate as well. Diffuse reflectance and absorption type near infrared systems probe a different part of the spectral response of the calibrator than does Raman scattering, but the calibrator of the invention could be suitable for both types of devices.

Tissue modulation in concert with difference spectroscopy and potentially other measurements isolates the spectroscopic signal from a particular component of the in vivo tissue. In this case, the sample, e.g. the capillary bed in a human fingertip or some other human tissue, is subjected to mechanical, thermal, and/or chemical stimuli chosen to induce specific spatio-temporal variations in tissue composition. For example, the mechanical response of mobile tissues such as blood and lymph to pressure far exceeds that of static structural tissues, and other bulk properties. Tissue modulation implies that the sample will be compared to itself as a part of the analog measurement process before, during, and after the stimulation. It is desirable for the calibrator to be compatible with the process and sample holder characteristics that are best suited to modulate the in vivo tissue.

Besides the specific requirements of device operation relating to laser operation and eye safety, there are other important requirements. Portable devices demand that we endeavor to keep the mechanics of initiating a calibration cycle instead of an in vivo measurement cycle transparent to the user. Lay people as well as the technically proficient should be able to use this process and device to facilitate confidence in the monitoring device. Moreover, system overhead can be reduced by avoiding front panel buttons and other higher-level input-output accessories. It is preferably easy and inexpensive to produce and dispose of many calibrators, as many may be needed.

The NIST Raman standard is designed for use by a technical professional, who would care for a primary standard calibrator more attentively than members of the general public using an at-home device for personal glucose monitoring.

SUMMARY OF THE INVENTION

The invention provides a calibrator suitable for calibrating a noninvasive analyte detector, such as a Raman spectroscopy device. The calibrator allows the user of the detection device to establish standard measurements of the analyte to be detected, thereby providing assurance that appropriate analyte measurements are obtained at the time of sampling. The calibrator is simple to use, making it suitable for home use by individuals regardless of medical or technical skill level. In particular, the calibrator can be used with a noninvasive glucose detection system, such as for monitoring of blood glucose levels in diabetics. For use with noninvasive detectors designed for obtaining measurements from a subject's fingertip, the calibrator can be formed into a shape that reasonably mimics a fingertip in size, texture and/or spectral properties.

In one embodiment, the calibrator comprises a body that contains a standard quantity of an analyte. The calibrator scatters near infrared radiation in the Mie limit, and is adapted to be apposed to an aperture of a spectrometer. In one embodiment, the calibrator body further comprises a gelatinous material comprising protein and carbohydrate. The viscoelastic properties of this gelatinous material allows it to be positioned near an aperture of a spectrometer in a manner similar to the positioning of a fingertip. This is particularly useful in systems in which the fingertip is pressed against a tissue modulator near the aperture to modulate blood flow in the region to be probed, as the calibrator can be pressed against the modulator in a similar fashion.

Optionally, the protein and carbohydrate-based calibrator further comprises a preservative. In addition, analyte particles to be suspended in the gel can be coated with a fatty acid to prevent contact between protein and sugar reactants in the gel, thereby suppressing Maillard chemistry that could alter spectroscopic features used in analyte quantification. The analyte particle coating can comprise mono-, di- and/or triglycerides and/or simple fatty acids. Examples of fatty acids include, but are not limited to, tristerin, stearic acid, oleic acid, trioleate and various mixed glycerides.

In an alternative embodiment, the calibrator body comprises a metal alkoxide derived gel. Such a sol-gel calibrator can be relatively rigid in form, and can be modified to facilitate positioning of the calibrator in the measurement device. For example, bumps, ridges and/or recesses in the surface of the calibrator can be designed to aide in alignment of the calibrator so that it is in register with an aperture. The calibrator can further comprise a coating applied to the surface of the body, wherein the coating comprises a sufficiently scattering medium to cause the calibrator to scatter near infrared radiation in the Mie limit. Optionally, the calibrator further comprises an absorbing layer applied to a sufficient portion of the surface of the body to absorb incident radiation passing through the body from an aperture of a spectrometer. Preferably, such an absorbing layer is between about 10 and about 100 microns thick. The absorbing layer typically comprises a fluorescent material or a non-emissive material.

Also provided is a method of producing a calibrator for use with a spectrometer. The method comprises selecting analyte particles, typically particles that are less than about 5 microns in size, and coating the analyte particles with a fatty acid. In some embodiments, the analyte particles are as small as about 0.5 microns in size. The method further comprises suspending the coated analyte particles in a gelatinous material comprising protein and carbohydrate, wherein the calibrator scatters near infrared radiation in the Mie limit.

In another embodiment, the method of producing a calibrator for use with a spectrometer comprises suspending the selected analyte particles in a sol-gel material, comprising a metal alkoxide derived gel to form a body. The method further comprises applying a coating to the surface of the body. The coating comprises a sufficiently scattering medium to cause the calibrator to scatter near infrared radiation in the Mie limit.

The invention additionally provides a method of calibrating a spectrometer. The method comprises positioning a calibrator of the invention in apposition to an aperture of the spectrometer and adjusting the spectrometer and/or a processing unit that communicates with the spectrometer to identify the standard quantity of the analyte present in the calibrator. These steps can be repeated with calibrators containing varying standard quantities of the analyte.

DESCRIPTION OF THE INVENTION

Figure 1:
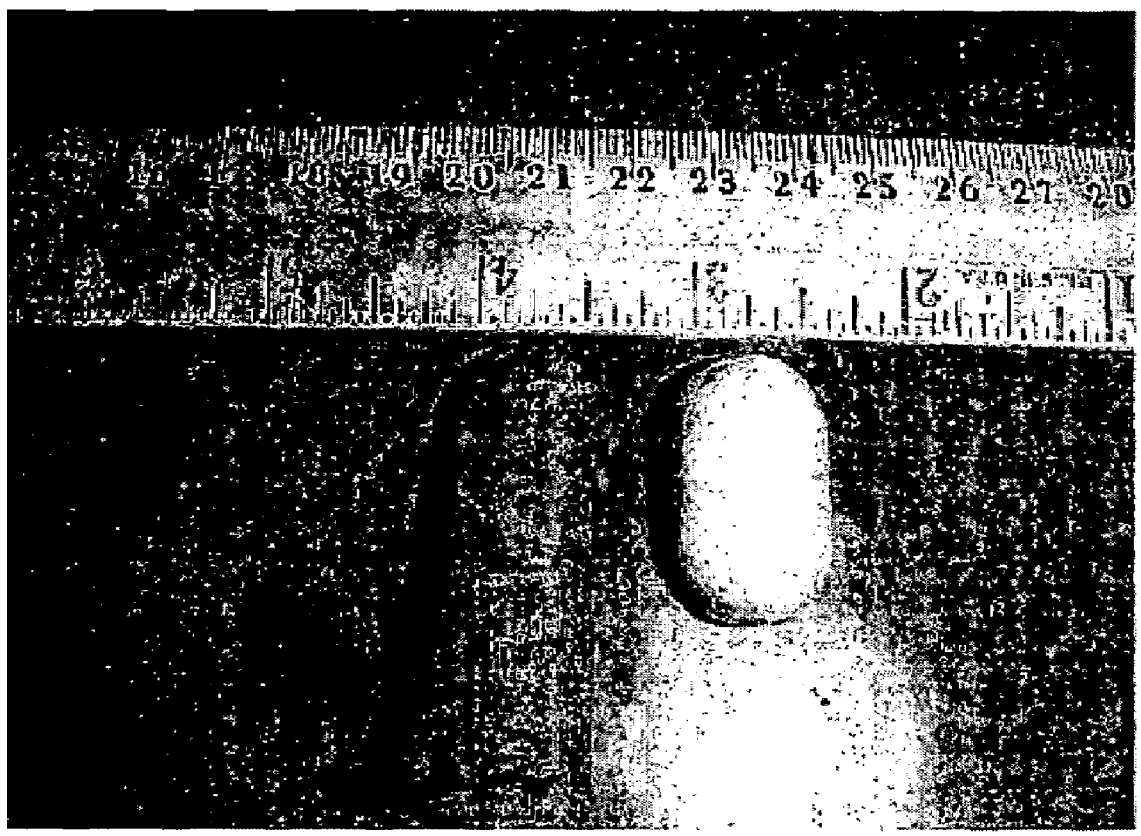
FIG. 1 illustrates one embodiment of a calibrator of the invention. The calibrator is shown next to a human fingertip and a ruler for perspective.

The invention is based on the discovery that an external calibration standard can be produced for use with a noninvasive analyte measurement device that provides an analyte reading that is stationary over time. The calibrator provides a standard for the analyte of interest, such as glucose, in a context that is analogous to the spectroscopic properties of a fingertip, as would be probed for noninvasive monitoring of blood glucose. This calibrator allows for better quantitative measures of performance of such invasive spectroscopic devices. In addition, the calibrator is easy and safe to use, making it suitable for use by the general public in both personal home-based and professional facility-based medical care.

The calibrator is particularly suited for use with a noninvasive spectrometer, such as the Raman spectrometer described in U.S. Pat. No. 6,044,285, issued Mar. 28, 2000; and U.S. Pat. No. 6,377,828, issued Apr. 23, 2002. In addition, the calibrator is compatible with methods and devices for tissue modulation in conjunction with spectroscopy, as described in U.S. Pat. No. 6,223,063, issued Apr. 24, 2001; U.S. Pat. No. 6,289,230, issued Sep. 11, 2001; and U.S. Pat. No. 6,292,686, issued Sep. 18, 2001. These devices and methods can be used for noninvasive quantification of blood glucose and other analytes.

Definitions

All scientific and technical terms used in this application have meanings commonly used in the art unless otherwise specified. As used in this application, the following words or phrases have the meanings specified.

As used herein, "Mie limit" refers to electromagnetic radiation interacting with materials having a characteristic size about equal to the wavelength of the electromagnetic radiation. Mie limit scattering typically occurs in the presence of scattering bodies that are approximately 50% of the size of an incident laser wavelength.

As used herein, "aperture" refers to an opening in a device through which light passes. The opening can be a physical opening, such as a hole in the device, or it can be merely an area that is sufficiently transparent to allow light to pass through. The aperture permits the direction of light onto a target or sample to be probed.

As used herein, "tissue" means any portion of an organ or system of the body, including, but not limited to, skin, capillary beds, blood, muscle, breast and brain.

As used herein, "Raman spectra associated with" a given component refers to those emitted Raman spectra that one skilled in the art would attribute to that component. One can determine which Raman spectra are attributable to a given component by irradiating that component in a relatively pure form, and collecting and analyzing the Raman spectra emitted by the component in the relative absence of other components.

As used herein, "tissue modulation" refers to the modulation of blood flow within a target tissue. The modulation achieves blood replete and blood depleted states within the target tissue.

As used herein, "blood replete" refers to a state in which blood flow through a tissue is unobstructed by, for example, vasoconstriction induced by cooling or the application of pressure. The blood replete state can be enhanced by conditions that increase vasodilation, such as warming.

As used herein, "blood depleted" refers to a state in which blood flow through a tissue is substantially restricted and blood volume is minimized. A blood depleted state can be achieved by, for example, cooling and/or applying pressure to the tissue.

As used herein, "portion of tissue" refers to an area of tissue that light penetrates, and from which a signal is collected. A "target tissue" refers to an area of tissue that is to be probed for signal collection.

Calibrator

1. Body of the Calibrator

The calibrator of the invention comprises a body that contains a standard quantity of an analyte. The calibrator scatters near infrared radiation in the Mie limit, and is adapted to be apposed to an aperture of a spectrometer. In some embodiments, this scattering is provided by the body itself.

There are many materials that could serve as the basis for a calibrator. The body can comprise materials derived from glasses, sol-gel systems, as well as protein and carbohydrate based gel systems. These latter systems are preferred for many uses because no part of the process, from handling of the precursors to disposing of old calibrator materials, requires regulatory assurances with regard to environmental or occupational safety concerns.

The composition of this material can be chosen from a wide variety of ingredients. Typical formulations include water, glycerin, glucose and other ingredients. Almost all these materials have a native auto-fluorescence matching that of in vivo tissue quite well. Experimentation has shown that use of standard preservatives imparts no unwanted Raman or fluorescence and can be incorporated with impunity. These additives are desirable in that an embodiment without the preservatives will develop a considerable amount of mold growth in a few days. Based on available water activity measurements as a function of glycerin content, a standard method of food science to quantify the action of added preservatives, such as glycerin, polysorbates and others, the invention has produced embodiments that are still good after 23 or more days. These additives can also impart a useful surface texture to the calibrator.

In one embodiment, the calibrator body further comprises a gelatinous material comprising protein and carbohydrate. The viscoelastic properties of this gelatinous material allows it to be positioned near an aperture of a spectrometer in a manner similar to the positioning of a fingertip. This is particularly useful in systems in which the fingertip is pressed against a tissue modulator near the aperture to modulate blood flow in the region to be probed, as the calibrator can be pressed against the modulator in a similar fashion.

Optionally, the protein and carbohydrate-based calibrator further comprises a preservative. In addition, analyte particles to be suspended in the gel can be coated with a fatty acid to prevent contact between protein and sugar reactants in the gel, thereby suppressing Maillard chemistry that could alter spectroscopic features used in analyte quantification. The analyte particle coating can comprise mono-, di- and/or triglycerides and/or simple fatty acids. Examples of fatty acids include, but are not limited to, tristerin, stearic acid, oleic acid, trioleate and various mixed glycerides.

In an alternative embodiment, the calibrator body comprises a metal alkoxide derived gel. One example of a material useful in the preparation of a sol-gel based calibrator is tetramethyl orthosilicate, or TMOS (Aldrich-Sigma, St. Louis, Mo.). Such a sol-gel calibrator can be relatively rigid in form, and can be modified to facilitate positioning of the calibrator in the measurement device. For example, bumps, ridges and/or recesses in the surface of the calibrator can be designed to aide in alignment of the calibrator so that it is in register with an aperture. The calibrator can further comprise a coating applied to the surface of the body to serve as a scattering layer, wherein the coating comprises a sufficiently scattering medium to cause the calibrator to scatter near infrared radiation in the Mie limit. Optionally, the calibrator further comprises an absorbing layer applied to a sufficient portion of the surface of the body to absorb incident radiation passing through the body from an aperture of a spectrometer. Preferably, such an absorbing layer is between about 10 and about 100 microns thick. The absorbing layer typically comprises a fluorescent material or a non-emissive material.

Metal alkoxide derived gel systems enjoy an advantage in durability. Calibrators for Raman spectroscopy of analytes other than glucose are typical candidates for use of sol-gel systems. Such a system is inherently less suitable for glucose calibration in a LighTouch™ format, however, as virtually all metal oxide sol-gel systems possess Raman features that interfere with the same glucose Raman features exploited to noninvasively measure blood glucose in invo.

Metal alkoxide based systems present a variety of other concerns as well. These involve quite messy and hazardous materials and specialized facilities for fabrication and disposal. For small amounts of devices, this would not be a problem, but over time, for many devices, these environmental considerations will become a significant factor in deciding the best course of action. The costs associated with these environmental issues could overwhelm all other costs in the limit of mass production.

The preferred embodiment (see FIG. 1) is a single protein-carbohydrate based gel-like material containing no extra layers as such. One might consider it to be something akin to uncooked dough. The material itself deforms under light pressure (0.1-3.0 Newtons; over the entire volar side capillary bed of a middle finger-see Table 1), i.e. tissue modulator appropriate pressure, almost identically to a real fingertip capillary bed. It can be cut and molded, i.e. kneaded, into whatever shape is most easily handled by the LighTouch™ operator, i.e. a trained technician or even a lay-person with or without diabetes.

TABLE 1

TEXTURE (TA-XT2) & Water Activity Measurements of Samples Tested

| | SAMPLE Arise 6000† + Dist. Water + Glycerine (grams) | Texture (TAXT-2) (Newtons) | Water Activity $(A_w)$* |
|---|---|---|---|
| 1. | Control$_1$ 5.0 + 3.0 + 0.0 | 0.690 | 0.740 |
| | Control 2 | | |
| 1a. | 5.0 + 4.0 + 0.0 | 0.628 | 0.988 |
| 2. | 5.0 + 3.5 + 0.5 | 0.477 | 0.914 |
| 3. | 5.0 + 3.0 + 1.0 | 1.120 | 0.874 |
| 4. | 5.0 + 2.0 + 2.0 | 1.145 | 0.738 |
| 5. | 5.0 + 1.0 + 3.0 | 1.239 | 0.575 |
| 6. | 5.0 + 0.0 + 4.0 | 2.459 | 0.347 |
| 7.** | 5.0 + 2.0 + 2.0 | 1.165 | 0.739 |

*Note:
Increasing levels of glycerine decreased the water activity ($A_w$ is a measure of available water for microbial growth. A lower number corresponds to a longer shelf life).
**Sample was still free of mold growth after 24 days.
†Arise 6000 is the trade name for the protein material used in a preferred embodiment.

2. Analytes

Because the monitoring of blood glucose is so important to the management of diabetes, glucose is an analyte of particular interest for use with the calibrator of the invention. Those skilled in the art will appreciate, however, that other analytes can be selected as the standard for calibration. Examples of analytes include, but are not limited to, glucose, lactate, urea, pyruvate, drugs, blood gases, total protein, free fatty acids, monoglycerides, diglycerides, triglycerides, creatinine, exchangeable protein associated amide protons or cholesterol.

The Maillard reaction is a significant factor in the operation of a gel-based calibrator. This reaction and the subsequent Amadori rearrangement complicate the preparation of calibration standards containing physiological concentrations of glucose. This reaction involves glucose and proteins and is the basis for the hemoglobin A1C test. The Maillard reaction involves glucose and other sugars reversibly reacting with certain amino acid side chains, e.g. lysine $NH_2$. Subsequently, the Maillard modified/damaged proteins can undergo the Amadori rearrangement irreversibly modifying the protein.

Once the Amadori rearrangement occurs, certain Raman spectroscopic feature(s) used to quantify glucose content become unusable. Thus it useful to understand the chemistry of glucose spiked protein based gels since they are essentially protein that is present in huge excess relative to the final desired sugar concentration, i.e. milimolar. To stabilize the small remaining glucose content ultimately desired, one can use ordinary encapsulation techniques in common usage in many food, pharmaceutical and cosmetic contexts. Note that one can employ glucose and other sugars without encapsulation, but their stability and shelf life may be reduced.

3. Scattering Properties

The calibrator, either as a property of the body of the calibrator or via a layer or coating, comprises a highly scattering medium, that causes the incident laser light to rapidly become spatially incoherent, thereby terminating or highly diminishing the propagation of incident laser light. The effect of this scattering is to minimize any directional bias of waste incident light that is collected by the optical system and imaged as very broadband background into the spectra. The scattering layer serves to present to the light collection system a similar Rayleigh background to what is presented by tissue in vivo.

The scattering effect can be designed to form spontaneously as a property of the body of the calibrator, or it can be added, e.g., as a layer, in a separate step. The scattering layer and the scattering properties of the body of the calibrator are maintained by the presence of fine particles and fibers, i.e. protein, lipid and carbohydrate, that scatter near infrared radiation in the Mie limit. The Mie limit corresponds to electromagnetic radiation interacting with materials having a characteristic size about equal to the wavelength of the electromagnetic radiation. Mie scattering shows a preference for forward scattering and this feature is important for calibrator design.

This implies that the fibers, particles, vesicles and other scattering bodies are roughly ±50% of the size of the incident laser wavelength, from about 200 nm in size to about 1.5 microns. These scattering centers occur naturally in certain materials, but can be added if required. Cellulose fibers, polymer fibers, quartz microspheres, e.g. Dupont's Ludox® line of materials, Intralipid® and other lipid-based vesical/micellular systems, and carbon fibers can be obtained commercially and can be used to establish the proper light scattering properties. Other additives that can be used include, but are not limited to, Cr(III), glucose, d2-glucose, albumin, urea, glutathione, cholesterol and triglycerides.

In a preferred embodiment, such as the protein/carbohydrate matrix approach, the scattering layer corresponds to both the outer layer of the calibrator and also the bulk of the underlying material to a depth of at least a few millimeters. In the case of a protein/carbohydrate matrix, the entire material already has the proper scattering properties and so nothing needs to be added and there is no physical differentiation between the body of the calibrator and the outer surface. In such an embodiment, the scattering layer is an integral feature of the body of the calibrator. The scattering layer also has the effect of keeping the incident radiation from producing unwanted reflections from either the front of the calibrator or from the back after penetrating the entire object.

Sol-gel materials produce beautiful, nearly transparent monoliths that allow light to pass completely through with very little spatial dispersion unless a scattering material is added (see the list above) to impart the effect. Without the added scattering layer, the incident light passes all the way through the calibrator and reflects off the fingers (or other object) holding it in place, causing an unpredictable and generally harmful succession of back reflections. Note that the scattering materials can be incorporated as a layer or simply dispersed through the bulk of the calibrator. When a layer is incorporated, it is typically more than approximately a few microns thick, but less than approximately 2 millimeters. Such a layer can be used on the front side of the calibrator, the rear side, or any combination thereof, all the way to a complete over-layer for the calibrator. Those skilled in the art will appreciate that the design depends on the geometry of the path of the incident laser, the relative position of the light detection and analysis system and the precise shape of the tissue modulator.

In some embodiments, the calibrator is a multi-layered object with varying fluorescence and Raman ratios. This object can be dragged across the aperture of the LighTouch™ tissue modulator or other device. The readings can be detected in real time by the LighTouch™ device, and the data interpreted by the controller, to yield a value for comparison to documentation that is provided with the calibrator. The approach effectively incorporates a low, medium and high analyte (e.g., glucose) standard in each calibrator. To work properly, the motion of the object across the aperture should be performed reproducibly.

4. Absorbing Layer

In some embodiments, the calibrator further comprises a dark absorbing coating on the body's outermost layer, away from the point where the incident light enters the calibrator. The absorbing layer terminates the entering laser beam. The incident light is thereby spatially dispersed at a point that is past the focal volume from which the Raman scattered light originates, and then mostly absorbed in this outermost layer. By dispersing the light first, the outermost layer will be able to absorb the incident light without excessive heating. This feature further minimizes the directional bias of waste incident light.

An absorbing layer is desirable when the scattering layer is not thick enough to effectively stop the incident radiation before it impinges on the backside of the calibrator. Such a layer is typically either fluorescent (porphyrin and derivatives) or totally non-emissive like black paint. Absorbing layers are employed on the backside of the calibrator so as not to interfere with entering light. An absorbing layer is typically ≈10-100 microns thick and need only cover a portion of the calibrator sufficient to contain the waste light.

Preparation of Calibrators

The approach involves grinding and sieving the (anhydrous) glucose particles to obtain the desired size distribution. There are various approaches to this step, including but not limited to, grinding and evaporation from solution. A rather small particle size is preferred, ideally ≈0.5 microns to ≈5.0 microns, since the glucose particles should be very small with respect to the size of the region probed by the instrument.

These particles can be coated using standard food science technology with mono-, di- and/or triglycerides and/or even simple fatty acids. Representative examples of these include tristerin, stearic acid, oleic acid and trioleate and various mixed glycerides. The fatty acids coat the particles in such a manner as to prevent contact between protein and sugar reactants, thereby suppressing Maillard chemistry. The choice of encapsulating material is based on considerations like preferred processing and storage temperatures, desired final shelf life, and desired final glucose concentration. The encapsulation adds to the net dilution factor and must be considered at various stages well known to the food processing industry. It is also well known to those skilled in the art that one can encapsulate using carbohydrates and other materials.

Embodiments based on sol-gel materials, which are rigid and not easily deformed, are preferably shaped to register with dimples and raised dots (as used in Braille) that are part of the tissue modulator surface. These raised dots are employed because they allow the user to locate their fingertip with respect to the tissue modulator orifice without visual inspection. These same dots will suffice to locate the calibrator body via the incorporation of reciprocating features on the calibrator body.

Sol-gel based materials have scattering layers and absorbing layers as described above and they can have scattering materials included into their body as were listed above. The protein based gel materials have the appropriate properties without requiring an added scattering layer. Matching the food mechanical properties (modulus of compression, tensile strength etc.) of the calibrator with those of the fingertip can be assessed using a food texture analyzer.

In one embodiment, de-mineralized gelatin, wherein metal ions, particularly Zn, Ca, Mg, Cr, Cu, Fe and others, are removed from gelatin precursor(s) can be used in the production of the calibrator. Such materials can be prepared by use of immobilized EDTA, or some other resin-based ion sequestering reagents. Or use of dialysis and unbound agents like EDTA to de-mineralize.

Additional Features

There are additional optional features that can be incorporated into the calibrator of the invention, as desired or suited to a particular application.

1. Safety Features

The calibrator can be prepared from edible materials as a safety feature. For example, some embodiments, e.g. sol-gel based calibrators, employ materials and produce structures that would be dangerous to eat (metal alkoxides, acids and/or bases). The organic additives used to counteract the brittleness of the pure sol-gel materials are toxic as well. One advantage the protein-based calibrator, for example, is its ease of handling, safety, cost, and overall environmentally friendly technology. The messy nature of the sol-gel calibrator and its deficiencies in terms of environmental and safety concerns, could ultimately render it more expensive. In addition, a coating or additive with an unpleasant taste or odor can be used to discourage people from putting the calibrator in their mouths.

2. Features to Prevent Misuse

The inclusion of a tiny amount of enzyme (e.g. trypsin, chymotrypsin, bromelain) that will very slowly undermine the mechanical integrity of the calibrator can be used to limit the shelf life of the calibrator. This strategy can be used to ensure that only sufficiently fresh calibrators are employed.

3. Features to Prolong Usable Life or Enhance Performance

Substances such as glycerin can be used to control water activity, and thereby control shelf life. Another strategy is to incorporate an antibacterial agent to extend shelf life.

As discussed above, one can encapsulate glucose and other precursors to limit the reactivity of components in the mixture (e.g. protein and glucose undergo Maillard reaction which, after Amadori rearrangement, yields glycated proteins lacking in vibrational spectral features needed for use of preferred algorithm used in calibration process). Encapsulation also allows attainment of low concentrations of glucose spectral features with accuracy, precision and stability. Encapsulation materials can include stearic acid and inert carbohydrate materials.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A calibrator comprising:
    a body comprising a standard quantity of an analyte, wherein the analyte comprises coated analyte particles suspended in a gelatinous material;
    wherein the calibrator scatters near infrared radiation in the Mie limit,
    wherein the calibrator is adapted to be apposed to an aperture of a spectrometer, the calibrator thereby external to in vito tissue.

2. The calibrator of claim 1, wherein the analyte is glucose.

3. The calibrator of claim 1, wherein said gelatinous material comprises a protein and a carbohydrate.

4. The calibrator of claim 3, wherein the gelatinous material further comprises a preservative.

5. The calibrator of claim 1, wherein the body further comprises a metal alkoxide derived gel.

6. The calibrator of claim 5, further comprising a coating applied to the surface of the body, wherein the coating comprises a sufficiently scattering medium to cause the calibrator to scatter near infrared radiation in the Mie limit.

7. The calibrator of claim 1, further comprising an absorbing layer applied to a sufficient portion of the surface of the body to absorb incident radiation passing through the body from an aperture of a spectrometer.

8. The calibrator of claim 7, wherein the absorbing layer is between about 10 and about 100 microns thick.

9. The calibrator of claim 7, wherein the absorbing layer comprises a fluorescent material or a non-emissive material.

10. The calibrator of claim 1, wherein the surface is modified to provide a detectable indication when it is registered with the aperture of a spectrometer.

11. The calibrator of claim 10, wherein the surface modification comprises bumps, ridges or recesses, and wherein the detectable indication is a resistance to movement upon registry with the aperture.

12. The calibrator of claim 1, wherein the coated analyte particles are coated with a fatty acid.

13. The calibrator of claim 12, wherein the fatty acid is tristerin, stearic acid, oleic acid, trioleate or a glyceride.

14. A method of calibrating a spectrometer, the method comprising:
    (a) positioning the calibrator of claim 1 in apposition to an aperture of the spectrometer; and
    (b) adjusting the spectrometer to identify the standard quantity of the analyte present in the calibrator.

* * * * *

UNITED STATES PATENT AND TRADEMARK OFFICE
CERTIFICATE OF CORRECTION

PATENT NO. : 7,664,605 B2  Page 1 of 1
APPLICATION NO. : 10/986673
DATED : February 16, 2010
INVENTOR(S) : Chaiken et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 760 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,664,605 B2  
APPLICATION NO. : 10/986673  
DATED : February 16, 2010  
INVENTOR(S) : Chaiken et al.

Page 1 of 1

It is certified that error appears in the above-identified patent and that said Letters Patent is hereby corrected as shown below:

Claim 1, Column 11, Line 16 delete "A calibrator" and insert --An external calibrator--.

Claim 1, Column 11, Line 25 delete "vito" and insert --vivo--.

Signed and Sealed this
Twenty-second Day of March, 2011

David J. Kappos
*Director of the United States Patent and Trademark Office*